(12) United States Patent
Zheng et al.

(10) Patent No.: US 9,168,283 B2
(45) Date of Patent: Oct. 27, 2015

(54) MEDEMIA NOBILIS EXTRACTS AND METHODS OF USE

(71) Applicant: Avon Products, Inc., Suffern, NY (US)

(72) Inventors: Qian Zheng, Morris Plains, NJ (US);
John W. Lyga, Basking Ridge, NJ (US);
Russell J. Wyborski, Pine Island, NY (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 13/710,617

(22) Filed: Dec. 11, 2012

(65) Prior Publication Data

US 2014/0161909 A1 Jun. 12, 2014

(51) Int. Cl.
*A61K 36/889* (2006.01)
*A61Q 19/08* (2006.01)
*A61K 8/97* (2006.01)

(52) U.S. Cl.
CPC .................. *A61K 36/889* (2013.01); *A61K 8/97* (2013.01); *A61Q 19/08* (2013.01); *A61K 2236/00* (2013.01)

(58) Field of Classification Search
CPC ................................ A61Q 19/00; A61Q 19/08
USPC .................................................... 424/725, 59
See application file for complete search history.

(56) References Cited

U.S. PATENT DOCUMENTS

| 8,394,427 B2 | 3/2013 | Zheng et al. |
| 8,771,758 B2 | 7/2014 | Ptchelintsev |
| 2006/0024390 A1* | 2/2006 | Schauss et al. ............... 424/727 |
| 2007/0224272 A1 | 9/2007 | Touitou |
| 2009/0301508 A1 | 12/2009 | Wang et al. |
| 2013/0053423 A1* | 2/2013 | Lyga ............................ 514/374 |

FOREIGN PATENT DOCUMENTS

| JP | 2000128730 A | 5/2000 |
| WO | 2004026249 A2 | 4/2004 |
| WO | 2009048282 A2 | 4/2009 |

OTHER PUBLICATIONS http://www.emedicinehealth.com/wrinkles/article_em.htm (2013).
Byers, H. Randolph; "Role of Cytoplasmic Dynein in Perinuclear Aggregation of Phagocytosed Melanosomes and Supranuclear Melanin Cap Formation in Human Keratinocytes," The Journal of Investigative Dermatology, vol. 121, No. 4, (2003).
U.S. Appl. No. 12/648,581, filed Dec. 29, 2009, Lyga, John W. et al.
U.S. Appl. No. 13/602,557, filed Sep. 4, 2012, Zheng, Qian et al.
U.S. Appl. No. 13/158,947, filed Jun. 13, 2011, Zheng, Qian et al.
U.S. Appl. No. 13/305,779, filed Nov. 29, 2011, Zheng, Qian et al.
U.S. Appl. No. 14/284,869, filed May 22, 2014, Ptchelintsev, Dmitri.
U.S. Appl. No. 13/216,626, filed Aug. 24, 2011, Thorn Leeson, Daniel.
U.S. Appl. No. 13/710,536, filed Dec. 11, 2012, Hwang, Cheng et al.
U.S. Appl. No. 14/066,862, filed Oct. 30, 2013, Lyga, John W. et al.
U.S. Appl. No. 14/055,037, filed Oct. 16, 2013, Khusial, Permanan Raaj.

* cited by examiner

*Primary Examiner* — Chris R Tate
*Assistant Examiner* — Randall Winston
(74) *Attorney, Agent, or Firm* — David M. Joyal; Joan M. McGillycuddy

(57) ABSTRACT

The present invention describes methods for improving the appearance of skin, particularly, treating, ameliorating, preventing, delaying, and/or improving one or more signs of aging, by topically applying compositions comprising an extract of *Medemia nobilis*.

18 Claims, 1 Drawing Sheet

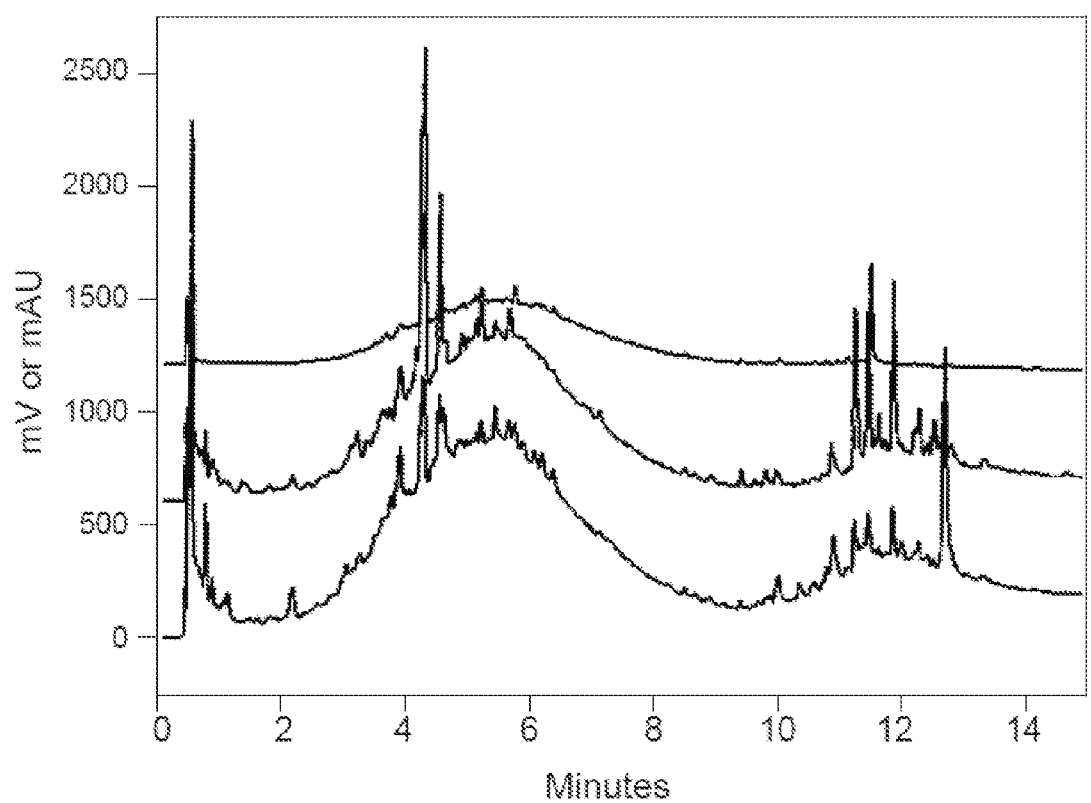

MEDEMIA NOBILIS EXTRACTS AND METHODS OF USE

RELATED APPLICATION

This application is filed concurrently with and claims priority to PCT Application Serial No. PCT/US12/68856, entitled "*Callistephus chinensis* extracts and methods of use"; PCT Application Serial No. PCT/US12/68858, entitled "*Serissa japonica* extracts and methods of use"; PCT Application Serial No. PCT/US/68862, entitled "Use of adipose septum protein modulators and compositions thereof"; PCT Application Serial No. PCT/US12/68863, entitled "Use of *Melicope* extracts to improve conditions caused by excess lipids"; PCT Application Serial No. PCT/US12/68865, entitled "*Hoya camosa* extracts and methods of use"; and U.S. application Ser. No. 13/710,585, entitled "*Maesa japonica* extracts and methods of use", the entirety of each of which is incorporated by reference in its entirety herein for all purposes. This application also incorporates by reference in their entirety for all purposes the following U.S. patent applications: U.S. application Ser. Nos. 13/305,779 and 13/216,626.

FIELD OF THE INVENTION

The present invention relates generally to compositions containing an extract of the *Medemia nobilis* plant for topical application to human integuments. In particular, the compositions of the present invention provide aesthetic and therapeutic benefits to the skin, in particular, by improving the condition and appearance of skin affected by signs of chronological, hormonal, or photo-aging.

BACKGROUND OF THE INVENTION

Consumers constantly seek to improve the appearance of their skin, and in particular seek to improve the appearance of skin by reducing signs of skin aging, such as wrinkles and the like. Cosmetic products that enhance the appearance of skin are increasingly in demand as consumers increasingly seek to mitigate or forestall signs of aging, in particular of wrinkles and/or fine lines. In particular, there is an interest in botanical and other naturally derived actives for cosmetic and therapeutic use on the skin.

It is therefore an object of the invention to provide new compositions and methods for combating signs of skin aging using botanical extracts. It is a further object of the invention to provide such compositions and methods to improve the overall appearance of skin, including treating, remediating, reversing, slowing, and/or preventing signs of aging, including signs of aging associated with degradation of collagen and/or elastin matrices and to enhance the regulation of new skin cells.

SUMMARY OF THE INVENTION

In accordance with the foregoing objectives and others, the present invention provides compositions containing an extract of the *Medemia nobilis* plant for topical application to the skin. The extract is typically from a protic solvent (e.g., ethanol or water). The extract can improve one or more signs of dermatological aging, most notably improvement in the appearance of wrinkles and/or fine lines, including the reversal of wrinkles and fine lines that have already formed.

While not wishing to be bound to any theory or mode of action, it was surprisingly discovered that extracts of *Medemia nobilis* stimulate the expression of key skin biomarkers associated with dermatological health. In particular, extracts of *Medemia nobilis* have surprisingly been found to enhance collagen production, improve hyaluronic acid levels, upregulate dynein, and promote cell proliferation.

*Medemia nobilis* is a species of a genus of flowering plants in the Arecaceae or Palmae family, native to Madagascar. *Medemia nobilis* has solitary, upright stems to 20 m tall and up to 35-45 cm in diameter, bulging at the base of the stem, covered with remnants of old leaf bases in young palms, then with irregular leaf scar rings and vertical fissures on a gray background in older ones. Its leaves are costapalmate, induplicate, up to 3 m across, divided into stiff, single-fold segments about ⅓ the length of the leaf blade, with bifid leaf segment tips. Staminate and pistillate flowers grow on separate palms. Fruits are oblong, ovoid, or spherical. Seeds are ridged and grooved. Any type of these plant parts are contemplated to be useful for preparing the extracts of the invention.

In one aspect of the invention, cosmetic compositions (or personal care products) are provided for improving one or more signs of dermatological aging in a cosmetically acceptable vehicle. In some embodiments, the *Medemia nobilis* extract, is an extract of the leaves, stems, seeds, and/or flowers (or combinations thereof) of the plant. In one aspect of the invention, the *Medemia nobilis* extract is a seed extract.

In some embodiments of the invention, methods for treating one or more signs of dermatological aging, comprising topically applying to skin in need thereof an effective amount an extract of *Medemia nobilis* in a cosmetically acceptable vehicle for a time sufficient to improve the appearance of said skin.

In another aspect, the invention relates to methods for improving the one or more signs of dermatological aging, such as wrinkles, comprising topically applying to the skin a cosmetic composition comprising an extract of *Medemia nobilis* in a cosmetically acceptable vehicle in an amount effective to stimulate procollagen, collagen, and/or Hyaluronic Acid (HA) production in the skin. In a further embodiment, a method for increasing skin cell proliferation is provided, comprising topically applying to skin in need thereof an effective amount of *Medemia nobilis* extract. In some embodiments, the *Medemia nobilis* extract is an aqueous and/or ethanol extract of the leaves, stems, seeds, and flowers of the plant, particularly the seeds. An effective amount of the extract of *Medemia nobilis* in a cosmetically acceptable vehicle can be applied to skin for a length of time sufficient to improve the appearance of the skin, typically daily applications for at least one week.

Compositions and methods are also provided for improving the aesthetic appearance of human skin comprising topically applying to an area of the skin in need thereof a composition comprising an extract of *Medemia nobilis*. The compositions typically will be formulated in a cosmetically acceptable vehicle, which will usually comprise an emulsion (e.g., water-in-oil or oil-in-water), stabilized with an emulsifier, and also will include other ingredients, such as skin actives (e.g., retinol, N-acetyl Tyrosinamide, etc.), antioxidants (e.g., TDPA), glycolic acid, preservatives, and the like. The compositions are topically applied to a human integument, such as the skin of the face, neck, lips, hands, chest, legs, scalp, etc., for a time sufficient to enhance the health or aesthetic appearance thereof, including reducing the number or severity of wrinkles and/or fine lines.

The composition will typically be applied to the skin one, two, or three times daily for as long as is necessary to achieve desired results. The treatment regiment may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, e.g., by visual inspection, or quantitatively, e.g., by microscopic or computer assisted measurements of wrinkle morphology (e.g., the number, depth, length, area, volume and/or width of wrinkles per unit area of skin). In one embodiment, the composition of the invention will be applied to the skin in an amount from about 0.001 to about 100 mg/cm$^2$, more typically from about 0.01 to about 20 mg/cm$^2$, and in one embodiment about 0.1 to about 10 mg/cm$^2$, in particular from about 1 to about 5 mg/cm$^2$, and ideally about 2 mg/cm$^2$.

These and other aspects of the present invention will be better understood by reference to the following detailed description.

DESCRIPTION OF THE DRAWINGS

FIG. 1 is an HPLC profile of an extract of *M. nobilis*

DETAILED DESCRIPTION OF THE INVENTION

Detailed descriptions of embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, and some features may be exaggerated to show details of one embodiment components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

All terms used herein are intended to have their ordinary meaning unless otherwise provided. By "cosmetically acceptable," it is meant that a particular component is generally regarding as safe and non-toxic at the levels employed. The term "prevent," as used herein, includes delaying the onset of or progression of a particular sign of skin aging. The term "thin skin" includes skin that becomes thinner with chronological aging as well as prematurely thinned skin, which may be caused, for example, by photo-aging. In one embodiment, the prematurely thinned skin has been diagnosed as such by a clinician. The phrase "individual in need thereof" refers to a human that could benefit from improved dermal appearance or health, including males or females. In the in one embodiment implementations of the invention, the compositions are applied to treat female skin. The individual in need thereof may be any age but will typically be a female aged 25-35 or 35-45 or 55-65 years old. The term "skin" includes, without limitation, the lips, skin of the face, hands, arms, neck, scalp, and chest. As used herein, the term "consisting essentially of" is intended to limit the invention to the specified materials or steps and those that do not materially affect the basic and novel characteristics of the claimed invention, as understood from a reading of this specification. As used herein, "% weight" or "% wt" refers to the weight percent of a component in relation to the total weight of the composition or formulation (i.e., including any carriers, vehicles, solvents, emollients, fillers, or other components added before application to the skin) unless otherwise specified.

The *Medemia nobilis* extracts of the invention may be used in cosmetic preparations and may be formulated with other cosmetically acceptable components, and vehicles, e.g. emulsions or serums, into a composition for topical application to the skin. The compositions will include other ingredients, such as, for example, alkylene oxide copolymer, emulsifiers, sunscreens, thickeners, botanicals, film formers, pH adjusters, fragrances, and preservatives. The compositions are topically applied to the skin in effective amounts, by which is meant an amount sufficient to achieve a measurable improvement in skin health or reduction in one or more dermatological signs of aging with daily (once, twice, etc.) administration, typically for a period of at least one week or more. Such signs of skin aging include without limitation, the following:
(a) treatment, reduction, and/or prevention of fine lines or wrinkles;
(b) reduction of skin pore size;
(c) improvement in skin thickness, plumpness, and/or tautness;
(d) improvement in skin smoothness, suppleness and/or softness;
(e) improvement in skin tone, radiance, and/or clarity;
(f) improvement in procollagen, and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) improvement of skin appearance decreased by aging and/or menopause;
(n) improvement in skin moisturization;
(o) increase in skin elasticity and/or resiliency;
(p) treatment, reduction, and/or prevention of skin sagging;
(q) improvement in skin firmness; and/or
(r) reduction of pigment spots and/or mottled skin.

In practice, the compositions of the invention, comprising *Medemia nobilis* extracts, in cosmetically acceptable vehicles, are applied to skin in need of treatment once or twice daily. That is, skin which suffers from a deficiency or loss in any of the foregoing attributes or which would otherwise benefit from improvement in any of the foregoing skin attributes. The treatment may continue for a week, two weeks, four weeks, eight weeks, six months or longer.

In one embodiment, the composition is intended for use as a non-therapeutic treatment. In another embodiment, the composition is an article intended to be rubbed, poured, sprinkled, or sprayed on, introduced into, or otherwise applied to the human body for cleansing, beautifying, promoting attractiveness, or altering the appearance, in accordance with the US FD&C Act, sec. 201(i).

In one embodiment the active agents are topically applied, in a cosmetically acceptable vehicle, to skin suffering from fine lines and/or wrinkles to prevent, treat, and/or amelioration the appearance of the fine lines and/or wrinkles in the skin. In this case, the compositions are applied to skin in need of treatment, by which is meant skin already having wrinkles and/or fine lines or skin that is at risk of developing fine lines and/or wrinkles. In one embodiment, the compositions are applied directly to the fine lines and/or wrinkles on the skin of the face, neck, lips, chest, and/or hands. The compositions may remediate or reverse signs of aging by enhancing production of elastin, collagen, and procollagen in skin, by enhancing the extracellular matrix, or by improving cell proliferation. Typically, one or more additional skin actives will be included, such as retinol, TDPA, glycolic acid, N-acetyl Tyrosinamide, other botanicals, and the like.

In one embodiment, the invention is directed to a method for improving the aesthetic appearance of human skin and/or improving the appearance of aged and/or photo-damaged skin by increasing the production of elastin, collagen, and procollagen in the skin, the method comprising topically applying to an area of the skin in need thereof an effective amount of a *Medemia nobilis* extract and a cosmetically acceptable vehicle.

The cosmetic compositions according to the invention can be formulated in a variety of forms for topical application and will comprise from about 0.001% to about 90% by weight of a *Medemia nobilis* extract, on an active weight basis, in one embodiment will comprise such *Medemia nobilis* extracts in an amount from about 0.01% to about 25% by weight, and more in one embodiment from about 0.05% to about 10% by weight. In some embodiments, the *Medemia nobilis* extracts will comprise from about 0.1% to about 5% by weight of the composition. In one embodiment, the *Medemia nobilis* extracts will comprise from about 0.075% to about 1.25% by weight of the composition.

The compositions can include a cosmetically acceptable vehicle. Such vehicles may take the form of any known vehicle in the art suitable for application to skin and may include, but are not limited to, water; vegetable oils; mineral oils; esters such as octal palmitate, isopropyl myristate, myristyl myristate, and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as dimethicone and cyclomethicone, hydrocarbon oils such as mineral oil, petrolatum, isoeicosane and (hydrogenated) polyisobutene; polyols such as propylene glycol, glycerin, butylene glycol, pentylene glycol, hexylene glycol, and caprylyl glycol; liposomes; waxes; or any combinations or mixtures of the foregoing.

The vehicle may comprise an aqueous phase, an oil phase, a glycerin phase, an alcohol, a silicone phase or mixtures thereof and may be in the form of an emulsion. Non-limiting examples of suitable emulsions include water-in-oil emulsions, oil-in-water emulsions, silicone-in-water emulsions, water-in-silicone emulsions, glycerin-in-oil emulsions, wax-in-water emulsions, water-oil-water triple emulsions or the like. The emulsion may include an emulsifier, such as a non-ionic, anionic or amphoteric surfactant, or a gelling agent.

A in one embodiment gelling agent is an ester terminated polyester amide (ETPEA), polyamide gelling agents, such as Ethylenediamine Hydrogenated Dimer Dilinoleate Copolymer bis-di-$C_{14-18}$ Alkyl Amide, Polyamide Resin, Dibutyl Lauryl Glutamide, Dibutyl Ethylhexanoil Glutamide, bentonite, or the like.

In some embodiments, the cosmetic composition further comprises at least one cosmetically acceptable preservative. Exemplary preservatives include, without limitation, EDTA, disodium EDTA, phenoxyethanol, methyl paraben, ethyl paraben, propyl paraben, imidazolidinyl urea, sodium dehydroacetate, para-hydroxybenzoic acid, hydantoin derivatives, propionate salts, quaternary ammonium compounds, benzyl alcohol, caprylyl glycol, butylated hydroxytoluene (BHT), and combinations thereof.

In one embodiment of the invention, the compositions may include additional skin actives, including but not limited to, retinoids (e.g., retinol, and the like), botanicals, keratolytic agents, desquamating agents, keratinocyte proliferation enhancers, collagenase inhibitors, elastase inhibitors, depigmenting agents, anti-inflammatory agents, steroids, anti-acne agents (e.g., salicylic acid, triclosan, and the like), antioxidants, desthiobiotin, piperazine carboxamide, $C_{12-15}$ alkyl benzoate, cis-6-nonenol, caffeine, arginine, glucosamine, algae extract, chlorphenesin, advanced glycation end-product (AGE) inhibitors, PLOD-2 stimulators (e.g., N-acetyl amino acid amides, such as N-Acetyl Tyrosinamide).

Suitable botanicals include, without limitation, *Abies pindrow, Abrus fruticulosus, Acacia catechu, Acacia melanoxylon, Alisma orientale, Amorphophallus campanulatus, Anogeissus latifolia, Archidendron clypearia, Asmunda japonica, Averrhoa carambola, Azadirachta indica, Berchemia lineate, Breynia fruticosa, Butea frondosa, Butea monosperma, Caesalpinia sappan Linn, Calatropis gigantean, Cayratia japonica, Cedrus deodara, Celosia argentea, Cistanche tubulosa, Clerodendron fragrans, Clerodendrum floribundum, Clinacanthus nutans, cola, Commersonia bartramia, Dendranthema indicum, Derris scandens, Desmanthus illinoensis, Dianella ensifolia, Dodonaea viscose, Duboisa myoporoides, Eclipta prostrate, Ehretia acuminate, Emblica officinalis, Erthrina Flabelliformis, Erythina indica, Fibraretinum resica Pierre, Ficus benghalensis, Ficus coronata, forskohlii, Ginkgo biloba, Glycyrrhiza glabra, Gomphrena globosa Linn, Goodenia ovata, Gynandropsis gynandra, hawthorne, Helichrysum Odoratissimum, Heliotropium indicum, Humulus japonicus, Hymenosporum flavum, Ilex purpurea Hassk, Innula racemosa, Ixora chinensis, Justicia ventricosa, Lavatera plebeian, Ligusticum chiangxiong, Ligusticum lucidum, Loropetalum chinense, Maesa japonica, Mallotus philippinensis, Mammea siamensis, Medemia nobilis, Melaleuca quinquernervia, Melicope hayesii, Mimusops elengi, Morinda citrifolia, Moringa oleifera, Naringi crenulata, Nerium indicum, Omolanthes populifolius, Operculina turpethum, Orthosiphon grandiflorus, Ozothamnus Obcordatus, Physalis minima, Portulaca oleracea, Pouzolzia pentandra, Psoralea corylifolia, Pteris semipinnata, Raphia farinifera, Sambucus chinensis, Sapindus rarak, Scoparis dulcis, Sesbania grandiflora, Stenoloma chusana, Tagetes erecta Linn, Terminalia bellerica, Tiliacora triandra*, tomato glycolipid, *Vernonia cinerea Linn. Less*, yohimbine, aloe, chamomile, and combinations thereof.

The composition may comprise additional active ingredients having anti-aging benefits, as it is contemplated that synergistic improvements may be obtained with such combinations. Exemplary anti-aging components include, without limitation, botanicals (e.g., *Butea frondosa* extract); phytol; thiodipropionic acid (TDPA) and esters thereof; retinoids (e.g., 9-cis retinoic acid, 13-cis retinoic acid, all-trans retinoic acid, derivatives thereof, and salts thereof, phytanic acid, retinol (Vitamin A) and esters thereof, such as retinol palmitate, retinol acetate and retinol propionate, and others); hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof, etc.), to name a few.

For use in the compositions of this disclosure, the plant, plant components, and/or active ingredients are in one embodiment derived directly from the plant. The components may be in a pure form, a semi-pure form, or unpurified form.

In in one embodiment, the extract of *Medemia nobilis* comprises an aqueous, alcoholic, or hydroalcoholic extract. In other embodiments, components are in the form of an extract obtained by polar protic solvent extraction, such as by using aqueous extraction, and ethanolic extraction, or a hydroalcoholic extraction.

Solvent extraction typically involves collecting the raw materials from the plant that contain the desired constituent(s), particularly above-ground parts, such as seeds, leaves, stems, flowers, bark, and the like, although in some cases, roots may also be useful. These plant materials may be dried and ground to small particle sizes, and then put into an extracting machine. Due to the difference in gravity and equilibrium, the solvent flows toward the raw material inlet, soaks the materials, and flows out from the opposite side of the solvent inlet. Since the plant materials and the solvent typically move in opposite directions against each other, the plant materials are constantly immersed in a solution that contains a low-concentration of extract. As a result of equilibrium, high yield of plant constituent(s) may be achieved by continuously extracting the plant material against the low-concentration solution. Of course, the foregoing is provided merely by example and is not meant to be limiting. The concentration of the plant material in a solvent extraction may be without limitation from about 5 g/L to about 50 g/L, in one embodiment from about 10 g/L to about 30 g/L, most in one embodiment at least 20 g/L.

Extraction time can be adapted to remove the desired plant constituents, for example between about 1-12 hours is typical, more in one embodiment being between about 2-6 hours, and most in one embodiment being between about 3-5 hours. The temperature of extraction can be chosen according to the solvent and the extraction method being used, but will typically be between about 20° C. to about 90° C. (including room temperature extraction), between about 40° C. to about 70° C., or between about 50° C. to about 60° C. The collected extract is typically fine-filtered to remove debris, and may be used directly, or may be concentrated, for example by distilling the solvent, by lyophilization, or by other conventional processing. The extract also can be provided in powder form by removal of substantially all of the solvent. The extract may be treated with activated charcoal or ion-exchange resins to remove impurities (e.g., poly phenols, color producing species, etc.)

A polar or aqueous solvent extraction method may involve washing and extracting the plant material using water, an aqueous solution, or other polar solvent. Non-limiting examples of polar solvents include, but are not limited to, water; alcohols (such as methanol, ethanol, propanol, ispropanol, butanol and the like); glycols (such as propylene glycol, and the like); ethers (such as diethyl ether, dipropyl ether, and the like); esters (such as butyl acetate, ethyl acetate, and the like); ketones (such as acetone, ethyl methyl ketone, and the like); organic acids including acetic acid, and the like; dimethyl sulfoxide; acetonitrile; other organic solvents; and combinations thereof. Other suitable solvents include physiological saline, phosphoric acid buffer and phosphate buffer saline and the like. In some in one embodiment embodiments, water is used as the polar solvent. Well-known methods in the art may be used for polar solvent extraction.

An organic solvent extraction method may involve washing and extracting the plant material using an organic solvent. Non-limiting examples of organic solvents include methanol, ethanol, isopropanol, ethyl acetate, dichloromethane, chloroform, hexane, xylene, and petroleum ether. Well-known methods in the art may be used for organic solvent extraction.

In some embodiments, the extraction comprises aqueous-organic extraction. Generally, aqueous-organic solvent extraction involves initially collecting raw materials from parts of the plant, particularly above-ground parts, such as leaves, stems, flowers, seeds, bark, and the like, which may be ground into small particle sizes. The ground plant material is soaked in aqueous solution that is acidic or alkaline, depending on the solubility and stability of the desired extract under neutral, acidic, or alkaline (basic) conditions. For extraction under acidic conditions, an acid such as hydrochloric acid or sulfuric acid may be added to water. For extraction under alkaline conditions, an alkali such as sodium hydroxide or sodium carbonate may be added to water. The extraction time and temperature of extraction are typically similar to that used in the organic solvent extraction method described above.

Typically, the extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated, or dried. Alternatively, organic solvent may be added to the neutralized solution to transfer the extract actives from an aqueous phase to an organic phase. Examples of such organic solvents include, but are not limited to, ethanol, isopropanol, butanol, pentanol, hexanol, and xylene. The extract comprising the transferred extract actives dissolved in organic solvent may be used directly, used as a concentrate, or dried.

The *Medemia nobilis* extract may be obtained by extracting *Medemia nobilis* leaves, seeds, flowers, and/or stems with water, ethanol, or a mixture thereof. The solvent systems may optionally comprise from about 5% by volume to about 95% by volume of ethanol, and from about 5% by volume to about 95% by volume of water; from about 10% by volume to about 90% by volume of ethanol, and from about 10% by volume to about 90% by volume of water; from about 25% by volume to about 55% by volume of ethanol, and from about 45% by volume to about 75% by volume of water.

Different plants containing different constituents may be mixed and extracted together. For example, *Medemia nobilis* may be co-extracted with another botanical. This process of mixed extraction in one embodiment is used if extracting two or more plants containing constituents having similar solubility in the solvent used for extraction, such as ethanol. The mixture of extracts may be concentrated and stored in an appropriate solvent.

In other embodiments, the *Medemia nobilis* extract, as referred to herein, includes "synthetic" extracts, i.e., where various combinations of known plant components and/or constituents are combined to substantially mimic the composition and/or activity of a plant extract of natural origin. Such synthetic extracts are included in the terms "extract" or "plant extract." The synthetic extracts will have two or more, three or more, or four or more active ingredients in common with a natural plant. Most in one embodiment, the synthetic extracts will have substantially the same number of active ingredients as a natural extract of the plant. The correspondence of the numerical incidence of active ingredients between the synthetic extracts and the plant or a natural plant extract may be described in terms of "percent commonality." In one embodiment, the synthetic extract has about 50% or more commonality to the chemical composition of a plant or natural plant extract. In other words, the synthetic extract has about 50% or more of the active ingredients found in the plant or a natural plant extract. More in one embodiment, the chemical composition of the synthetic extract has about 70% or more commonality to the chemical composition of a plant or a natural plant extract. Optimally, a synthetic extract has about 90% or more commonality to the chemical composition of a plant or a natural plant extract. The plant or natural plant extract for comparison is derived, for example, from the *Medemia nobilis* plant, e.g., as described herein.

The *Medemia nobilis* plant may be in any form including, but not limited to, the whole plant, a dried plant, a ground plant, or parts thereof, including but not limited to, seeds, needles, leaves, roots, bark, cones, stems, rhizomes, callus cells, protoplasts, organs and organ systems, and meristems, an extract, a dried extract, a synthetic extract, or components and/or constituents found in, or isolated from, the plant, and/or portions of the plant, or extracts derived either directly or synthetically from the plant, or any combinations thereof.

In certain embodiments, the cosmetic composition comprises an amount of *Medemia nobilis* extract from about 0.001 weight % to about 50 weight based on the total weight of the composition; in one embodiment from about 0.01 weight % to about 25 weight % based on the total weight of the composition; more in one embodiment from about 0.05 weight % to about 10 weight % based on the total weight of the composition, and even more in one embodiment from about 0.1 weight % to about 1 weight %, or about 0.5 weight %, based on the total weight of the composition. In one embodiment, a cosmetic composition comprises an amount of *Medemia nobilis* extract from about 0.01 weight % to about 5 weight % based on the total weight of the composition. The above amounts refer to an "active amount" of *Medemia nobilis* extract. The term "active amount" refers to the amount of *Medemia nobilis* extract to the concentration of the material absent diluent, solvent, carrier, filler or the like.

Another aspect of the instant invention relates to cosmetic use of compositions comprising a *Medemia nobilis* extract. The extract is believed to remediate, reverse, reduce, ameliorate, forestall, or prevent dermatological signs of aging.

Generally, the improvement in the condition and/or aesthetic appearance is selected from the group consisting of: reducing dermatological signs of chronological aging, photoaging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof.

"Treatment" as used herein, as well as related terms such as "treat" or "treating," refers to eradicating, reducing, ameliorating, or reversing one or more of the unwanted features associated with the skin condition being treated, such that the consumer or clinician perceives an improvement in the appearance of the skin or other treatment benefit with respect to the condition. "Prevention" as used herein, as well as related terms such as "prevent" or "preventing," refers to affording skin not yet affected by the condition a benefit that serves to avoid, delay, forestall, minimize, or reduce the recurrence one or more unwanted features associated with the skin condition to be prevented. Such preventative benefits include, for example, delaying development and/or recurrence of the condition, or reducing the duration, severity, or intensity of one or more unwanted features associated with the condition if it eventually develops.

In some embodiments, the cosmetic compositions can further comprise at least one collagen and/or elastin stimulator. Such collagen or elastin stimulators are effective in, for example, providing improvement in procollagen and/or collagen production and/or improvement in maintenance and remodeling of elastin. A compound or substance is determined to be a collagen and/or elastin upregulator by, for example, assaying keratinocytes and/or fibroblasts of the skin and determining whether the candidate substance upregulates cellular mRNA encoding collagen and/or elastin.

In accordance with the invention, the *Medemia nobilis* extracts may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. In one embodiment the composition is formulated as an emulsion, lotion, cream, ointment, serum or gel.

In addition, the compositions contemplated may include one or more compatible cosmetically acceptable adjuvants commonly used and known by the skilled practitioner, such as colorants, fragrances, emollients, humectants, preservatives, vitamins, chelators, thickeners, and the like, as well as other botanicals such as aloe, chamomile, and the like.

In some embodiments, the topical formulation comprises a cosmetically acceptable vehicle (medium, diluent, or carrier) that is compatible with human skin. The cosmetically acceptable vehicle may comprise an aqueous phase, an oil phase, alcohol, or aqueous/alcohol-based solutions, ointments, lotions, gels, wax-in-water emulsions, or water-in-oil, oil-in-water, or water-oil-water emulsions, e.g., having the appearance of creams, gels, microemulsions, or aerosols.

The aqueous phase may be a mixture of one or more water soluble or water dispersible substances, which can be liquid, semi-solid or solid at room temperature (25° C.). The vehicle comprises, or can be in the form of, a suspension, dispersion, or solution in water or in an aqueous-alcoholic vehicle, which may contain a thickener or gellant. A person skilled in the art can select the appropriate cosmetic form, the ingredients contained therein, as well as the method for preparing it, on the basis of the knowledge that the skilled artisan possesses.

In some embodiments, the cosmetically acceptable vehicle may include an aqueous phase which may contain water, or a mixture of water and at least one hydrophilic organic solvent, in particular an alcohol, especially a linear or branched lower mono alcohol containing from 2 to 5 carbon atoms, e.g., ethanol or propanol; a polyol, e.g., propylene glycol, sorbitol, glycerol, diglycerol, panthenol, or polyethylene glycol; and mixtures thereof. This aqueous phase may represent from about 0.5 weight % to about 99.99 weight %, based upon the total weight of the composition.

In some embodiments, when the composition of the invention is in the form of an emulsion, the composition may also optionally comprise a surfactant, in one embodiment in an amount from about 0.1 weight % to about 30 weight %, and in particular, from about 1 weight % to about 20 weight %, based upon the total weight of the composition. In one embodiment, the emulsifier will be present in an amount from about 1% to about 10% by weight. The emulsifier may comprise, for example, lecithin and/or a polyalkoxylated polymer, such as silicone copolyol.

In some embodiments, the composition may also comprise a thickening polymer such as an amphiphilic polyurethane, a polyacrylic homopolymer or copolymer, a polyester, and/or a hydrocarbon-based resin. The thickener may also be a natural hydrocolloid, such as xantan gum, guar gum, and the like.

The invention also contemplates formulations that may comprise an oil phase containing oil-soluble or oil-dispersible substances, which are liquid at room temperature (25° C.) and/or oily or waxy substances that are solid at room temperature, such as waxes, semi-solids, gums, and mixtures thereof. The waxes can include hydrocarbon-based waxes, fluoro waxes and/or silicone waxes and can be of plant, mineral, animal, and/or synthetic origin. Formulations typically comprise from about 1 weight % to about 20 weight % waxes, based upon total weight. The gums, if used, are generally high molecular weight cyclic polydimethylsiloxanes (PDMS), cellulose gums or polysaccharides, and the semi-solid materials are generally hydrocarbon-based compounds, such as, but not limited to, lanolins and derivatives thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, com oil, soybean oil, grapeseed oil, castor oil, avocado oil, caprylic/capric acid triglycerides, or jojoba oil; linear or branched hydrocarbons of mineral or synthetic origin, such as liquid paraffins and derivatives thereof, or petroleum jelly; synthetic esters and ethers, in particular esters of fatty alcohols, namely, for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polydimethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of about 0 weight % to about 90 weight %, in one embodiment from about 1 weight % to about 80 weight % by weight of the oil phase.

The oil phase of the formulation may also comprise one or more cosmetically acceptable organic solvents. If present, these solvents will typically be present in an amount of from about 0.1 weight % to about 60 weight %, in one embodiment from about 1 weight % to about 30 weight %, based Gn the total weight of the composition, and may be selected from the group consisting of lipophilic organic solvents, amphiphilic organic solvents, and mixtures thereof. Suitable solvents which may be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof. In some other embodiments, the compositions can be in the form of vesicular dispersions containing ionic and/or nonionic lipids, as described above.

In yet other embodiments, the compositions are formulated into liposomes or microspheres, which can comprise other additives or substances, and/or which can be modified to more specifically target or remain at a site following administration. (See, e.g., U.S. Pat. No. 5,770,222 to Unger et al., incorporated herein by reference.)

The formulations for use in the inventive methods may further comprise any ingredient conventionally used in the cosmetics field. These ingredients include, e.g., preserving agents, aqueous phase thickeners (polysaccharide biopolymers, synthetic polymers), fatty-phase thickeners, fragrances, hydrophilic and lipophilic active agents, and mixtures thereof. The amounts of these various ingredients are those conventionally used in the cosmetics field to achieve their intended purpose, and range typically from about 0.01 weight % to about 20 weight %, based upon the total weight of the composition or formulation. The nature of these ingredients and their amounts will be selected to be compatible with the production and intended applications of the compositions, as described herein.

In some embodiments, the formulation may optionally comprise an additional particulate phase, typically present in an amount of from about 0.01 weight % to about 30 weight %, based upon the total weight of the composition or formulation, in one embodiment from about 0.1 weight % to about 20 weight %, and which can comprise pigments and/or pearlescent agents and/or fillers used in cosmetic compositions.

Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminum lakes and carbon black. Suitable pearlescent agents include mica coated with titanium oxide, with iron oxide, or with natural pigment. Fillers, if used, will typically be in an amount from about 0.1 weight % to about 20 weight %, based on the total weight of the composition or formulation, in one embodiment from about 1 weight % to about 10 weight %. Suitable fillers include talc, silica, zinc stearate, mica, kaolin, nylon (in particular orgasol) powder, polyethylene powder, TEFLON™, starch, boron nitride, copolymer micro spheres such as Expancel (Nobel Industrie), Polytrap (Dow Corning), and silicone resin microbeads (Tospearl from Toshiba).

In some embodiments, the topical formulations may also include one or more antioxidants. An antioxidant functions, among other things, to scavenge free radicals from skin, protecting the skin from environmental aggressors. Examples of antioxidants that may be used in the present compositions and formulations include compounds having phenolic hydroxy functions, such as ascorbic acid and its derivatives/esters; thiodipropionic acid and its esters; vitamins A, C, or E; polyphenols, beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant in one embodiment from about 0.001 weight % to about 10 weight %, and more in one embodiment from about 0.01 weight % to about 5 weight %, based on the total weight of the composition or formulation.

In some embodiments, the topical formulations may also include one or more of the following: a skin penetration enhancer, an emollient, a skin plumper, an exfoliation promoter, and an optical diffuser. Details with respect to these and other suitable cosmetic ingredients can be found in the *International Cosmetic Ingredient Dictionary and Handbook,* 10th Edition (2004), published by the Cosmetic, Toiletry, and Fragrance Association (CTFA), at pp. 2177-2299, which is herein incorporated by reference in its entirety.

An emollient provides the functional benefits of enhancing skin smoothness and may aid in improving the appearance of skin affected by aging. Examples of emollients include isopropyl myristate, petrolatum, isopropyl lanolate, silicones (e.g., methicone, dimethicone), oils, mineral oils, fatty acid esters, or any mixtures thereof. The emollient is in one embodiment present from about 0.1 wt % to about 50 wt % of the total weight of the composition or formulation.

A skin plumper serves as a collagen enhancer to the skin. An example of a suitable, and in one embodiment, skin plumper is palmitoyl oligopeptide. Other skin plumpers are collagen and/or glycosaminoglycan (GAG) enhancing agents. The skin plumper is in one embodiment present from about 0.1 weight % to about 20 weight % of the total weight of the composition or formulation.

In another embodiment, the topical compositions of the present invention may also include one or more of the following: a skin penetration enhancer, a humectant, such as glycerin or caprylyl glycol, a sunscreen, such as avobenzone, an exfoliating agent, and/or an antioxidant.

In some embodiments, formulations may have one or more exfoliation promoters. Suitable examples of exfoliation promoters include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The in one embodiment exfoliation promoters are 3,6,9-trioxaundecanedioic acid, glycolic acid, lactic acid, or any mixtures thereof. When an embodiment of the invention includes an exfoliation promoter, the formulation may have from about 0.1 weight to about 30 weight %, in one embodiment from about 1 weight % to about 15 weight %, and more in one embodiment from about 1 weight % to about 10 weight %, of the exfoliation promoter based on the total weight of the composition or formulation.

An optical diffuser is a particle that changes the surface optometrics of skin, resulting in a visual blurring and softening of, for example, lines and wrinkles, as well as lumpiness and unevenness caused by cellulite and other unwanted subcutaneous fat. Examples of optical diffusers that can be used in the present invention include, but are not limited to, boron nitride, mica, nylon, polymethylmethacrylate (PMMA), polyurethane powder, sericite, silica, silicone powder, talc, TEFLON™, titanium dioxide, zinc oxide, or any mixtures thereof. The optical diffuser is in one embodiment present from about 0.01 weight % to about 20 weight %, based on the total weight of the composition or formulation.

In some embodiments, formulations may have one or more retinoids. Exemplary retinoids include, without limitation, retinoic acid (e.g., all-trans or 13-cis), derivatives thereof, and salts thereof, retinaldehyde, retinol (Vitamin A) and esters thereof, such as retinyl palmitate, retinyl acetate and retinyl propionate.

In some embodiments, formulations may have one or more sunscreen protectors. A sunscreen protects the skin from damaging ultraviolet rays. In an illustrative embodiment of the invention, the sunscreen would provide both UV A and UVB protection, by using either a single sunscreen or a combination of sunscreens. Among the sunscreens that can be employed in the present compositions are avobenzone, cimlamic acid derivatives (such as octylmethoxy cinnamate), octyl salicylate, oxybenzone, titanium dioxide, zinc oxide, or any mixtures thereof. The sunscreen may be present in an amount from about 1 weight % to about 30 weight of the total weight of the composition. More typically, the sunscreens will comprise from about 2.5% to about 20% by weight of the composition. The compositions of the invention having sunscreen bring about additional improvements to the aesthetic appearance of skin, including at least one of the following: minimizing sun-burning and/or reducing redness.

In some embodiments, the formulation may also have one or more of the following cosmetic and pharmaceutical active agents, excipients, ingredients, or adjuvants: anesthetics; antibiotics, e.g., erythromycins and tetracyclines; salicylic acids; anti-allergenics; antifungals; antiseptics; anti-irritants; anti-inflammatory agents; antimicrobials; analgesics; nitric oxide synthase inhibitors; insect repellents; self-tanning agents; skin penetration enhancers; skin cooling agents; chelating agents; colorants including dyes, lakes and pigments that may be untreated or chemically surface treated to improve wetability or some other property; demulcents; emulsifiers; fragrances; humectants; lubricants; skin protectants; moisturizers; pH adjusters; preservatives; stabilizers; surfactants; thickeners; film formers; plasticizers; viscosity modifiers; vitamins; blood flow stimulators; or any mixtures thereof. The amounts of these various substances are those that are conventionally used in the cosmetic or pharmaceutical fields to achieve their intended purposes, for example, they may constitute from about 0.01 weight % to about 20 weight % of the total weight of the composition or formulation.

Emulsifiers are typically present in the compositions or formulations of the invention in an amount from about 0.01% to about 30%, and in one embodiment from about 0.5% to about 30%, most in one embodiment from about 1% to about 10%, based on the total weight of the composition. In some other embodiments, the composition or formulation is free or substantially free of emulsifiers.

Non-limiting examples of suitable thickening agents include xanthan gum, hydroxypropyl cellulose, hydroxyethyl cellulose, carbomer, gum acacia, Sepigel 305 (available from Seppic Co., France), and clays such as magnesium aluminum silicate.

The topical compositions of the present invention may include, and their utility can be enhanced, by one or more humectants, such as ureas, pyrrolidine carboxylic acids, amino acids, sodium hyaluronates, certain polyols, and other compounds with hygroscopic properties.

The general activity and mildness to skin of compositions according to the invention can also be enhanced by neutralization to a pH from about 2 to about 8, with a pH in the range of from 3 to 7 being in one embodiment. In some embodiment, the composition will have a pH in the range of from 3.5 to 5.5. Suitable pH adjusters is accomplished using one or more of adjusters, such as ammonium chloride, ammonium hydroxide, potassium hydroxide, sodium hydroxide, arginine or other amino acids, citric acid, hydrochloric acid, lactic acid, and/or triethanolamine, to bring the pH within the desired range.

It is also contemplated that the compositions of the invention will be useful for treating thin skin by topically applying the composition to thin skin of an individual in need thereof. "Thin skin" is intended to include skin that is thinned due to chronological aging, menopause, or photo-damage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals. The methods may be used to treat men and women. In some embodiments, the methods are employed to treat wrinkles in female skin, such as skin of the face.

EXAMPLES

The following examples describe specific aspects of the invention to illustrate the invention but should not be construed as limiting the invention, as the examples merely provide specific methodology useful in the understanding and practice of the invention and its various aspects.

Example 1

In Vivo Up-Regulation of Key Skin Biomarkers

Botanical extracts of *Medemia nobilis* were tested for the ability to upregulate key skin biomarkers in vivo. 20 healthy female Caucasian subjects aged 30-65 with skin type II or III and mild to moderate photo damage were treated with ingredients on the dorsal forearm for 3 weeks (3 consecutive rounds of 5×24 hour patches under semi-occlusion). Test articles and vehicles were applied in a randomized allocation on five sites on each forearm. Each subject was treated with the extract of *Medemia nobilis* at a concentration of 0.2% formulated in Propylene Glycol/Ethanol/H$_2$O (65:25:10) vehicle and the vehicle control. The application dose was 2 mg/cm$^2$. After treatment, a 2 mm punch biopsy was obtained from each treatment site and fixed in 10% buffered formalin. Tissue samples were then embedded in paraffin, sectioned (5 micrometer thickness), processed and stained for the following skin markers—Collagen (by Masson Trichrome), Procollagen, Ki-67 as marker for proliferation, Hyaluronic acid (HA) and Dynein. For each marker, the treated site was compared to the vehicle site to determine the difference in the intensity of the marker. If the intensity of the marker in the treated site is higher relative to control, it indicates improvement of that biomarker. Table 1 shows the percent of subjects that had an improvement in the tested skin biomarkers after three weeks of treatment with an extract of *Medemia nobilis*.

TABLE 1

Percent of subjects that had an improvement in the tested skin biomarkers after three weeks of treatment with an extract of *Medemia nobilis*.

|  | Collagen | Procollagen | Ki67 | HA | Dynein |
| --- | --- | --- | --- | --- | --- |
| *Medemia nobilis* | 45.0 | 44.4 | 63.2 | 38.9 | 26.3 |

As shown in Table 1, the botanical extract of *Medemia nobilis* upregulates key biomarkers, such as Collagen, Procollagen, Ki-67, Hyaluronic acid, and dynein in vivo when topically applied to skin. It is believed that up-regulation of these biomarkers, which decline in aging skin, leads to an improvement to the appearance of aging skin.

Example 2

Up-Regulation of Dyneins

Botanical extracts of *Medemia nobilis* were tested for the ability to upregulate dynein. The dynein modulation assay was carried out as follows. Normal human dermal fibroblasts or keratinocytes were cultured in 96-well tissue culture treated plates, containing appropriate culture medium. Stock solution of *Medemia nobilis* extracts were made in an appropriate vehicle (water/Ethanol/Propylene glycol). Cells were treated with test material or respective vehicle control diluted in growth medium for 24 hours in a humidified 37° C. incubator with 10% CO$_2$. After incubation, growth medium from each plate was removed and 100 μL of lysis buffer was added to the wells and placed in 37° C. incubator with 10% CO$_2$ for 30 minutes. At the end of incubation, the cells are collected in freezer plates and placed in −80° C. freezer, until analysis. Changes in mRNA for Dynein after treatment were analyzed using Panomics Quantigene multiplex assay that employs a branched DNA technology, following manufacturer's instructions (Affymetrix, Calif.). Percent increase (up-regulation) in mRNA for the heavy chain DYNC1H1 of cytoplasmic dynein was calculated by comparing the test results to the control. The percent up-regulation is converted to a scaled score as shown below in Table 2.

TABLE 2

| % Up-regulation | Up-regulation Scale |
| --- | --- |
| 0-20 | 0 |
| 21-40 | + |
| 41-60 | ++ |
| 61-80 | +++ |
| >81 | ++++ |

The concentrations of the *Medemia nobilis* extract is provided based on the dry weight of the plant extract, by which is meant the weight of the extract after volatile extraction solvents have been removed. The cells tested were either keratinocytes (K) or fibroblasts (F). The results are provided below in Table 3.

TABLE 3

| Plant Extract | Conc. (%) | Cell Type | Effect |
| --- | --- | --- | --- |
| *Medemia nobilis* | 0.01 | K | ++++ |

Example 3

Wrinkle Cream

| | |
|---|---|
| *Medemia nobilis* extract | 0.1-10% |
| Water | |
| Cyclopentasiloxane | |
| Glycerin | |
| Ethylhexyl methoxycinnamate | |
| Ammonium glycolate | |
| Glycolic acid | |
| Propylene glycol | |
| Bis-PEG/PPG-14/14 dimethicone | |
| Cetearyl methicone | |
| Ethoxydiglycol | |
| *Punica granatum* fruit juice | |
| Thiodipropionic acid | |
| Ammonium trioxaundecanedioate | |
| Trioxaundecanedioic acid | |
| Hydrolyzed *hibiscus esculentus* extract | |
| *Foeniculum vulgare* (fennel) fruit extract | |
| *Medicago sativa* (alfalfa) extract | |
| *Daucus carota sativa* (carrot) root extract | |
| *Cocos nucifera* (coconut) fruit juice | |
| Hydrolyzed wheat protein | |
| *Olea europaea* (olive) leaf extract | |
| *Pyrus malus* (apple) root extract | |
| *Aesculus hippocastanum* (horse chestnut) seed extract | |
| *Pichia* peptone filtrate | |
| *Saccharomyces* ferment filtrate | |
| Yeast extract | |
| *Panax ginseng* root extract | |
| *Padina pavonica* extract | |
| Lecithin | |
| Glycogen | |
| Atelocollagen | |
| Biotin | |
| Methicone | |
| Mannitol | |
| *Tilia cordata* wood extract | |
| Calcium pantothenate | |
| C30-45 alkyl cetearyl | |
| Dimethicone/polycyclohexene oxide crosspolymer | |
| Cetyl PEG/PPG-10/1 dimethicone | |
| Dimethicone/vinyl dimethicone crosspolymer | |
| Silica | |
| Paraffin | |
| Butylene glycol | |
| Xanthan gum | |
| Caprylyl glycol | |
| PEG-40 hydrogenated castor oil | |
| Sodium chondroitin sulfate | |
| Talc | |
| Hexylene glycol | |
| Fragrance | |
| Iron oxides | |

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 4

Hand Cream

| | |
|---|---|
| *Medemia nobilis* extract | 0.1-10% |
| Octinoxate | 0.1-15% |
| Oxybenzone | 0.1-15% |
| Avobenzone | 0.1-15% |
| Water | |
| Glycerin | |
| Pentaerythrityl tetraethylhexanoate | |
| Steareth-2 | |
| Glycolic acid | |
| Behenyl alcohol | |
| Dimethicone | |
| PEG-40 stearate | |
| Myristyl myristate | |
| Trisiloxane | |
| Lauryl lactate | |
| Aspartic acid | |
| *Zea mays* (corn) kernel extract | |
| Phytol | |
| *Butyrospermum parkii* (shea) butter | |
| *Cola nitida* seed extract | |
| *Glycine soja* (soybean) seed extract | |
| *Punica granatum* fruit juice | |
| Retinyl palmitate | |
| *Daucus carota sativa* (carrot) root extract | |
| Ascorbyl palmitate | |
| *Helianthus annuus* (sunflower) seed extract | |
| Retinol | 0.001-10% |
| *Glycine soja* (soybean) oil | |
| *Saxifraga sarmentosa* extract | |
| *Vitis vinifera* (grape) fruit extract | |
| Tocopherol | |
| Beta-carotene | |
| *Morus nigra* root extract | |
| *Scutellaria baicalensis* root extract | |
| Glyceryl stearate | |
| PEG-100 stearate | |
| PVM/MA decadiene crosspolymer | |
| Xanthan gum | |
| Silica | |
| Acrylates/carbamate copolymer | |
| Maltodextrin | |
| Lecithin | |
| Trimethylsiloxysilicate | |
| Butylene glycol | |
| Ammonium hydroxide | |
| Phenoxyethanol | |
| Methylparaben | |
| Disodium EDTA | |
| BHT | |
| Fragrance | |

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 5

Wrinkle Cream

| | |
|---|---|
| *Medemia nobilis* extract | 0.1-10% |
| Water | |
| Glycerin | |
| Ethylhexyl isononanoate | |
| Octyldodecanol | |
| Dimethicone | |
| Butylene glycol | |
| Polymethyl methacrylate | |
| Trisiloxane | |
| Hydroxyethyl acrylate/sodium acryloyldimethyl taurate copolymer | |

Isohexadecane
Acetyl tyrosinamide
Dimethiconol
PEG-100 stearate
Laureth-4
Polysorbate 60
Polysorbate 20
Ascorbic acid
BHT
Sodium hydroxide
Disodium EDTA
Retinol
Phenoxyethanol
Methylparaben The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 6

Face Cream

| | |
|---|---|
| *Medemia nobilis* extract | 0.1-10% |
| Water | |
| Glycerin | |
| Cetearyl alcohol | |
| Butylene glycol | |
| Neopentyl glycol diheptanoate | |
| *Butyrospermum parkii* (shea) butter | |
| Hydrogenated polyisobutene | |
| Petrolatum | |
| Dilauryl thiodipropionate | |
| *Perilla ocymoides* seed oil | |
| Polymethyl methacrylate | |
| *Melicope hayesii* leaf extract | |
| *Malus domestica* fruit cell culture extract | |
| Mesyloxybenzyl isobutylbenzene sulfonamide | |
| Thiazolylalanine | |
| *Saccharomyces* ferment lysate filtrate | |
| Palmitoyl tetrapeptide-10 | |
| Palmitoyl tetrapeptide-7 | |
| Palmitoyl oligopeptide | |
| *Foeniculum vulgare* (fennel) fruit extract | |
| *Coffea arabica* (coffee) seed oil | |
| *Coffea arabica* (coffee) seed extract | |
| *Ilex paraguariensis* leaf extract | |
| Ceramide 2 | |
| *Crataegus monogyna* fruit extract | |
| Phytol | |
| Tocopherol | |
| Cetearyl glucoside | |
| Behenyl alcohol | |
| Ceteareth-20 | |
| Diazolidinyl urea | |
| Ozokerite | |
| Hydroxyethyl acrylate/sodium acryloyldimethyl taurate copolymer | |
| Carbomer | |
| Isohexadecane | |
| Potassium hydroxide | |
| Disodium EDTA | |
| Thiodipropionic acid | |
| Polysorbate 60 | |
| Glyceryl acrylate/acrylic acid copolymer | |
| C12-15 alkyl benzoate | |
| Tribehenin | |
| Xanthan gum | |

Caprylyl glycol
PEG-60 almond glycerides
PEG-10 rapeseed sterol
Cetyl hydroxyethylcellulose
Lecithin
Steareth-20
Caramel
Yellow 5/CI 19140

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 7

Night Cream

| | |
|---|---|
| *Medemia nobilis* extract | 0.1-10% |
| Water | |
| Glycerin | |
| Caprylic/capric triglyceride | |
| Glycolic acid | |
| Hydrogenated polydecene | |
| Ethylhexyl isononanoate | |
| Myristyl myristate | |
| Trioxaundecanedioic acid | |
| Behenyl alcohol | |
| Cetyl alcohol | |
| Glyceryl stearate | |
| Dimethicone | |
| Hydroxyethyl acrylate/sodium acryloyldimethyl taurate copolymer | |
| Carrageenan | |
| Propylene glycol stearate | |
| Thiodipropionic acid | |
| Nonenol | |
| *Sapindus rarak* fruit extract | |
| *Pouzolzia pentandra* extract | |
| Methoxybenzoyl methylsulfonyl oxopiperidinyl carboxamide | |
| Thiazolylalanine | |
| *Punica granatum* sterols | |
| *Glycine soja* (soybean) sterols | |
| *Butyrospermum parkii* (shea) butter | |
| Polysorbate 60 | |
| PEG-75 stearate | |
| Ceteth-20 | |
| Steareth-20 | |
| Hydrogenated lecithin | |
| Isohexadecane | |
| Choleth-24 | |
| Maltodextrin | |
| Chimyl alcohol | |
| Ceteth-24 | |
| Sorbitan isostearate | |
| Batyl alcohol | |
| Ammonium hydroxide | |
| Disodium EDTA | |
| Phenoxyethanol | |
| Methylparaben | |
| Propylparaben | |
| Fragrance | |

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 8

Day Cream

| | |
|---|---|
| *Medemia nobilis* extract | 0.1-10% |
| Octinoxate | 0.1-15% |
| Octisalate | 0.1-15% |
| Oxybenzone | 0.1-15% |
| Avobenzone | 0.1-15% |
| Water | |
| Glycerin | |
| Silica | |
| Dimethicone | |
| Stearic acid | |
| Stearyl alcohol | |
| Nonenol | |
| *Sapindus rarak* fruit extract | |
| *Pouzolzia pentandra* extract | |
| Methoxybenzoyl methylsulfonyl oxopiperidinyl piperazinecarboxamide | |
| Thiazolylalanine | |
| *Saccharomiyces*/platinum ferment | |
| Trisiloxane | |
| Dimethiconol | |
| Myristyl myristate | |
| Maltodextrin | |
| PEG-100 stearate | |
| Caprylyl glycol | |
| Glyceryl stearate | |
| Sodium polyacrylate | |
| Polyurethane-40 | |
| Potassium hydroxide | |
| Acrylates/C10-30 alkyl acrylate crosspolymer | |
| Disodium EDTA | |
| 1,2-hexanediol | |
| Fragrance | |
| Phytol | |
| Biosaccharide gum-1 | |
| Dilauryl thiodipropionate | |
| Dimethicone crosspolymer | |
| Silica | |
| Pentaerythrityl tetraethylhexanoate | |
| Bis-PEG-18 methyl ether dimethyl silane | |
| PEG-40 stearate | |
| Steareth-2 | |
| Polysorbate 60 | |
| Sorbitan isostearate | |
| PEG-20 methyl glucose sesquistearate | |
| Carbomer | |
| Acrylates/C10-30 alkyl acrylate crosspolymer | |
| Hydroxyethyl acrylate/sodium acryloyldimethyl taurate copolymer | |
| Phenoxyethanol | |
| Caprylyl glycol | |
| Disodium EDTA | |
| Sodium hydroxide | |

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 9

Night Cream

| | |
|---|---|
| *Medemia nobilis* extract | 0.1-10% |
| Water | |
| Glycerin | |
| Butylene glycol | |
| Dimethicone | |
| SD alcohol 40-B | |
| Isohexadecane | |
| Isododecane | |
| Aluminum starch octenylsuccinate | |
| *Pouzolzia pentandra* extract | |
| *Sapindus rarak* fruit extract | |
| Nonenol | |
| Methoxybenzoyl methylsulfonyl oxopiperidinyl piperazinecarboxamide | |
| Maltodextrin | |
| Thiazolylalanine | |
| Palmitoyl lysyl aminovaleroyl lysine | |

Example 10

Body Lotion

| | |
|---|---|
| *Medemia nobilis* extract | 0.1-10% |
| Water | |
| Petrolatum | |
| Lactic acid | |
| Glycerin | |
| Stearic acid | |
| Isopropyl palmitate | |
| Ethylhexyl methoxycinnamate | |
| Glycol stearate | |
| Dimethicone | |
| *Theobroma cacao* (cocoa) seed butter | |
| Sodium PCA | |
| Urea | |
| *Oryza sativa* (rice) bran oil | |
| *Simmondsia chinensis* (jojoba) seed oil | |
| Hydrogenated polyisobutene | |
| Bisabolol | |
| *Glycine soja* (soybean) sterols | |
| Lecithin | |
| *Glycine soja* (soybean) oil | |
| Magnesium aluminum silicate | |
| PEG-100 stearate | |
| Ammonium hydroxide | |
| Glyceryl stearate | |
| Xanthan gum | |
| Disodium EDTA | |
| Phenoxyethanol | |
| Ethylene brassylate | |
| Fragrance | |

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 11

Day Cream

| | |
|---|---|
| *Medemia nobilis* extract | 0.1-10% |
| Octinoxate | 0.1-15% |
| Octisalate | 0.1-15% |
| Oxybenzone | 0.1-15% |
| Avobenzone | 0.1-15% |
| Homosalate | 0.1-15% |
| Water | |
| Dimethicone | |
| Isodecyl isononanoate | |
| Glycerin | |
| Butylene glycol | |
| HDI/trimethylol hexyllactone crosspolymer | |
| Hydroxyethyl acrylate/sodium acryloyldimethyl taurate copolymer | |
| Dilauryl thiodipropionate | |
| Polymethyl methacrylate | |
| Thiodipropionic acid | |
| Salicylic acid | |
| *Eclipta prostrata* extract | |
| *Gossypium herbaceum* (cotton) extract | |
| Palmitoyl tetrapeptide-7 | |
| Sodium hyaluronate | |
| *Phyllanthus emblica* fruit extract | |
| *Foeniculum vulgare* (fennel) seed extract | |
| Yeast extract/extrait de levure | |
| *Saccharomyces* lysate extract | |
| *Kaempferia galanga* root extract | |
| *Saccharomyces* ferment filtrate | |
| Dimethicone crosspolymer | |
| Sorbitan isostearate | |
| Silica | |
| Steareth-20 | |
| Lactoferrin | |
| Phospholipids | |
| Isohexadecane | |
| Hydrogenated lecithin | |
| Phenoxyethanol | |
| Acrylates/C10-30 alkyl acrylate crosspolymer | |
| Carbomer | |
| Tromethamine | |
| Polysorbate 60 | |
| Methylparaben | |
| Disodium EDTA | |
| Propylparaben | |
| Fragrance | |
| Mica/CI 77019 | |
| Titanium dioxide/CI 77891 | |

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 12

Day Cream

| | |
|---|---|
| *Medemia nobilis* extract | 0.1-10% |
| Octinoxate | 0.1-15% |
| Octisalate | 0.1-15% |
| Oxybenzone | 0.1-15% |
| Avobenzone | 0.1-15% |
| Water | |
| Dimethicone | |
| Glycerin | |
| Butylene glycol | |
| Isodecyl isononanoate | |
| Tromethamine | |
| Dilauryl thiodipropionate | |
| Phytol | |
| Thiodipropionic acid | |
| Thiazolylalanine | |
| *Sesbania grandiflora* flower extract | |
| *Amorphophallus campanulatus* rhizome/root extract | |
| *Punica granatum* fruit juice | |
| Palmitoyl lysyl aminovaleroyl lysine | |
| Tocopherol | |
| Polysorbate 20 | |
| Cetearyl alcohol | |
| *Kaempferia galanga* root extract | |
| Isohexadecane | |
| Carbomer | |
| Acrylates/C10-30 alkyl acrylate crosspolymer | |
| Nylon-12 | |
| Polymethylsilsesquioxane | |
| Hydroxyethyl acrylate/sodium acryloyldimethyl taurate copolymer | |
| Xanthan gum | |
| Ceteareth-20 | |
| Hydrogenated lecithin | |
| Silica | |
| Polysorbate 60 | |
| Trimethylsiloxysilicate | |
| Sorbitan isostearate | |
| Dimethicone crosspolymer | |
| Polymethyl methacrylate | |
| Ethylhexylglycerin | |
| Disodium EDTA | |
| Phenoxyethanol | |
| Fragrance | |

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 13

Sunscreen Body Lotion

| | |
|---|---|
| *Medemia nobilis* extract | 0.1-10% |
| Homosalate | 0.1-15% |
| Octisalate | 0.1-15% |
| Oxybenzone | 0.1-15% |
| Avobenzone | 0.1-15% |
| Octocrylene | 0.1-15% |
| Water | |
| Isododecane | |
| Barium sulfate | |
| Propanediol | |
| Cetyl dimethicone | |
| Silica | |
| Styrene/acrylates copolymer | |
| Aluminum starch octenylsuccinate | |
| Hydroxyethyl urea | |
| Choleth-24 | |
| Dilauryl thiodipropionate | |
| *Kaempferia galanga* root extract | |
| *Glycine soja* (soybean) seed extract | |
| Oryzanol | |

(Avobenzone 0.1-15% appears in continued column)

-continued

Phaeodactylum tricornutum extract
Foeniculum vulgare (fennel) fruit extract
Daucus carota sativa (carrot) root extract
Tocopherol
Dimethicone crosspolymer
Urea
Glycerin
Caprylic/capric triglyceride
Cetyl PEG/PPG-10/1 dimethicone
Hydroxyethyl acrylate/sodium acryloyldimethyl taurate copolymer
Ceteth-24
Phenoxyethanol
Isohexadecane
Sodium citrate
VP/eicosene copolymer
Caprylyl glycol
PEG-8 laurate
Disodium EDTA
Xanthan gum
Polysorbate 60
Citric acid
Isoceteth-20
Calcium chloride
Fragrance The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 14

Night Cream

| | |
|---|---|
| *Medemia nobilis* extract | 0.1-10% |
| Water | |
| Dimethicone | |
| Glycerin | |
| Butylene glycol | |
| Glycolic acid | |
| Behenyl alcohol | |
| Hydrogenated polyisobutene | |
| Hydroxyethyl acrylate/sodium acryloyldimethyl taurate copolymer | |
| Trisiloxane | |
| Isohexadecane | |
| Cetearyl alcohol | |
| Thiodipropionic acid | |
| Phenyl trimethicone | |
| Pentaerythrityl tetraethylhexanoate | |
| *Vitis vinifera* (grape) fruit cell extract | |
| *Malus domestica* fruit cell culture extract | |
| *Eclipta prostrata* extract | |
| Palmitoyl lysyl aminovaleroyl lysine | |
| Palmitoyl tetrapeptide-10 | |
| Palmitoyl tetrapeptide-7 | |
| *Melicope hayesii* leaf extract | |
| *Saccharomyces* ferment lysate filtrate | |
| Thiazolylalanine | |
| Mesyloxybenzyl isobutylbenzenesulfonamide | |
| Phytol | |
| Isomalt | |
| PEG-150 distearate | |
| Polysorbate 60 | |
| Cetearyl glucoside | |
| Dimethiconol | |
| PEG-100 stearate | |
| Lecithin | |

-continued

Steareth-20
Sodium polyacrylate
Silica
Xanthan gum
Ammonium hydroxide
Phenoxyethanol
Disodium EDTA
Fragrance
Caramel
Red 4/CI 14700

The above formula is prepared with an aqueous extract of *Medemia nobilis* seed. The example is repeated with an ethanolic extract of *Medemia nobilis*. The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin Example 15

Eye Cream

| | |
|---|---|
| *Medemia nobilis* extract | 0.1-10% |
| Water | |
| Glycerin | |
| *Butyrospermum parkii* (shea butter) | |
| Cyclopentasiloxane | |
| Cetearyl alcohol | |
| Ethylhexyl palmitate | |
| Glyceryl stearate | |
| PEG-100 stearate | |
| PEG-40 stearate | |
| *Theobroma cacao* (cocoa) seed butter | |
| Butylene glycol | |
| Palmitoyl oligopeptide | |
| Ceramide 2 | |
| *Glycine soja* (soybean) seed extract | |
| Yeast extract/extrait de levure | |
| *Saccharomyces* lysate extract | |
| Glucosamine HCL | |
| *Punica granatum* fruit juice | |
| *Helianthus annuus* (sunflower) seed extract | |
| Hydrolyzed milk protein | |
| Phytol | |
| Ascorbyl palmitate | |
| Retinyl palmitate | |
| Tocopherol | |
| Urea | |
| Panthenol | |
| Tocopheryl acetate | |
| Algae extract | |
| Squalane | |
| Sorbitan tristearate | |
| Stearic acid | |
| Hydrogenated polyisobutene | |
| Dimethicone | |
| Tribehenin | |
| PEG-10 rapeseed sterol | |
| C12-15 alkyl benzoate | |
| Silica | |
| Carbomer | |
| Hydroxyethyl acrylate/sodium acryloyldimethyl taurate copolymer | |
| Polymethyl methacrylate | |
| Sodium hydroxide | |
| Phenoxyethanol | |
| Polysorbate 60 | |
| BHT | |
| Phosphoric acid | |
| Methylparaben | |
| Disodium EDTA | |

-continued

Propylparaben
Mica
Titanium dioxide

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 16

Skin Discoloration Cream

| | |
|---|---|
| *Medemia nobilis* extract | 0.1-10% |
| Water | |
| Isopropyl myristate | |
| Myristyl myristate | |
| Petrolatum | |
| PEG-8 | |
| Propylene glycol | |
| Ethylhexyl methoxycinnamate | |
| Glyceryl stearate | |
| PEG-100 stearate | |
| Cetyl alcohol | |
| Magnesium aluminum silicate | |
| Dimethicone | |
| Choleth-24 | |
| Thiodipropionic acid | |
| Panthenol | |
| Retinyl palmitate | |
| *Saxifraga sarmentosa* extract | |
| *Vitis vinifera* (grape) fruit extract | |
| Tocopherol | |
| *Morus nigra* root extract | |
| *Scutellaria baicalensis* root extract | |
| Tocopheryl acetate | |
| Ceteth-24 | |
| Hydroxyethyl cellulose | |
| Citric acid | |
| Sodium citrate | |
| Fragrance | |
| Disodium EDTA | |
| Benzyl alcohol | |
| Imidazolidinyl urea | |
| BHT | |

The above formula is prepared with an aqueous extract of *Medemia nobilis* seed. The example is repeated with an ethanolic extract of *Medemia nobilis*.

The above formula is applied to the skin once or twice daily for a period of at least three weeks. Improvements in collagen and procollagen levels of at least 20%, 25%, 30%, 35%, or even 40%, or more, are achieved, as compared to the baseline levels prior to treatment, or of similar untreated areas of skin.

Example 17

Exemplary HPLC Protocol

Extracts were generally characterized by high performance liquid chromatography. A sample size of approximately 5 mg/mL was dispersed in 25/75 MeOH/H$_2$O and sonicated. The characterization was performed on a Zorbax SBC-18 column (7.5 cm×4.6 mm, 3.5 um particle size) and detection was achieved using diode array UV absorbance, 260 nm 300 nm and 360 nm, with lines on FIG. 1 depicted in ascending order and 260 nm on bottom. Operating conditions were flow rate 1.5 ml/min; temperature, 40° C.; sample injection volume, 20 μL, and time of run, 19 minutes. The mobile phase gradient used was as follows. In one embodiment, the extracted composition of the present invention, in substantial isolation, exhibits an HPLC profile substantially similar to that depicted in FIG. 1.

TABLE 4

| Mobile Phase Gradient | |
|---|---|
| Time | Phase |
| 0 Minutes: | 15% Methanol(Solvent B)/85% Water with 1% acetic acid (Solvent A) |
| 10 Minutes: | 95% Methanol/5% Water with 1% Acetic acid. |
| 15 Minutes: | 15% Methanol/85% Water with 1% Acetic acid. |
| 15.01 Minutes: | 95% Methanol/5% Water with 1% Acetic acid. |
| 19 Minutes: | 15% Methanol/85% Water with 1% Acetic acid |

Example 18

Preparation of *Medemia nobilis* Extract

Preparation of *Medemia nobilis* extract is generally described in U.S. patent application Ser. Nos. 13/305,779 and 13/216,626, filed on Dec. 30, 2010 and Aug. 24, 2011, respectively, and herein incorporated by reference in their entirety. *Medemia nobilis* leaves and stems are extracted with water/ethanol, and filtered to generate a *Medemia nobilis* raw extract. The extract is then concentrated to aqueous suspension, which is let stand overnight at 4 C. The concentrated aqueous suspension is then precipitated and filtered with solid fraction removed, yielding a filtered aqueous filtered solution. Butanol is then added to the filtered aqueous suspension, then a liquid/liquid extraction is performed with subsequent removal of the organic phase. The remaining aqueous phases is then concentrated, dried, and irradiated to yield a dried purified *Medemia nobilis* extract, which may then be resuspended for further use (in one embodiment, as an aqueous resuspension).

A HPLC trace of a representative *Medemia nobilis* extract is found at FIG. 1.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A composition for stimulating collagen, pro-collagen or hyaluronic acid production in the skin of a subject, said composition comprising from 0.075% to 1.25% by weight of a protic solvent extract of *Medemia nobilis*, a cosmetically acceptable vehicle, and a preservative selected from the group consisting of disodium EDTA, phenoxyethanol, methyl paraben, ethyl paraben, propyl paraben, imidazolidinyl urea, sodium dehydroacetate, para-hydroxybenzoic acid, hydantoin derivatives, propionate salts, quaternary ammonium compounds, benzyl alcohol, an butylated hydroxytoluene (BHT).

2. The composition according to claim 1, wherein said cosmetically acceptable vehicle comprises from about 2% to about 98% by weight water.

3. The composition according to claim 1, wherein said preservative comprises disodium EDTA.

4. The composition according to claim 1, wherein said preservative comprises phenoxyethanol.

5. The composition according to claim 1, wherein said preservative comprises methyl paraben.

6. The composition according to claim 1, wherein said preservative comprises ethyl paraben.

7. The composition according to claim 1, wherein said preservative comprises propyl paraben.

8. The composition according to claim 1, wherein said preservative comprises imidazolidinyl urea.

9. The composition according to claim 1, wherein said preservative comprises sodium dehydroacetate.

10. The composition according to claim 1, wherein said preservative comprises para-hydroxybenzoic acid.

11. The composition according to claim 1, wherein said preservative comprises propionate salts.

12. The composition according to claim 1, wherein said preservative comprises quaternary ammonium compounds.

13. The composition according to claim 1, wherein said preservative comprises benzyl alcohol.

14. The composition according to claim 1, wherein said preservative comprises butylated hydroxytoluene (BHT).

15. The composition according to claim 1, wherein said preservative comprises hydantoin derivatives.

16. The composition according to claim 1, wherein said vehicle is in the form of an emulsion stabilized with an emulsifier.

17. The composition according to claim 1, wherein said composition further includes an ingredient selected from retinoids, N-acetyl tyrosinamide, thiodipropionic acid (TDPA), glycolic acid, and salicylic acid.

18. The composition according to claim 1, wherein said protic solvent extract is an ethanolic extract.

* * * * *